United States Patent
Deng et al.

(10) Patent No.: US 12,350,263 B2
(45) Date of Patent: *Jul. 8, 2025

(54) DOSING AND EFFECT OF C5a ANTAGONIST WITH ANCA-ASSOCIATED VASCULITIS

(71) Applicant: CHEMOCENTRYX, INC., San Carlos, CA (US)

(72) Inventors: Jun Deng, Cupertino, CA (US); Petrus Bekker, Los Altos, CA (US); Jan Hillson, Seattle, WA (US)

(73) Assignee: CHEMOCENTRYX, INC., Thousand Oaks, CA (US)

( * ) Notice: Subject to any disclaimer, the term of this patent is extended or adjusted under 35 U.S.C. 154(b) by 767 days.

This patent is subject to a terminal disclaimer.

(21) Appl. No.: 17/519,266

(22) Filed: Nov. 4, 2021

(65) Prior Publication Data
US 2022/0296576 A1 Sep. 22, 2022

Related U.S. Application Data

(63) Continuation of application No. 16/433,487, filed on Jun. 6, 2019, now Pat. No. 11,191,756.

(60) Provisional application No. 62/682,013, filed on Jun. 7, 2018.

(51) Int. Cl.
| | |
|---|---|
| A61K 31/445 | (2006.01) |
| A61K 9/00 | (2006.01) |
| A61K 31/52 | (2006.01) |
| A61K 31/675 | (2006.01) |
| C07K 16/28 | (2006.01) |
| A61K 31/573 | (2006.01) |

(52) U.S. Cl.
CPC .......... *A61K 31/445* (2013.01); *A61K 9/0053* (2013.01); *A61K 31/573* (2013.01); *A61K 31/675* (2013.01); *C07K 16/2887* (2013.01)

(58) Field of Classification Search
CPC .. A61K 31/445; A61K 31/573; A61K 31/675; A61K 9/0053; C07K 16/2887
See application file for complete search history.

(56) References Cited

U.S. PATENT DOCUMENTS

| | | | |
|---|---|---|---|
| 11,191,756 | B2 | 12/2021 | Deng et al. |
| 2008/0188528 | A1 | 8/2008 | Biediger et al. |
| 2011/0275639 | A1 | 11/2011 | Fan et al. |
| 2017/0283446 | A1 | 10/2017 | Fan et al. |
| 2019/0134020 | A1 | 5/2019 | Deng et al. |

FOREIGN PATENT DOCUMENTS

| | | |
|---|---|---|
| WO | 2006/128670 A1 | 12/2006 |
| WO | 2010/075257 A1 | 7/2010 |
| WO | 2011/163640 A1 | 12/2011 |
| WO | 2016/053890 A1 | 4/2016 |
| WO | 2016/166357 A2 | 10/2016 |
| WO | 2016/166357 A3 | 10/2016 |

OTHER PUBLICATIONS

International Search Report mailed Jan. 7, 2019 corresponding to PCT/US2018/058134 filed Oct. 30, 2018; 12 pages.
International Search Report mailed Jul. 30, 2019 corresponding to PCT/US2019/035758 filed Jun. 6, 2019; 18 pages.
International Preliminary Report on Patentability (Chapter II) mailed Mar. 17, 2020 corresponding to PCT/US2019/035758 filed Jun. 6, 2019; 17 pages.
European Search Report mailed Jul. 6, 2021 corresponding to EP 18873880.1 filed Oct. 30, 2018; 9 pages.
Proposed INN: List 114 Avacopan https://www.who.int/medicines/publications/druginformation/innlists/PL114.pdf?ua=1 International Nonproprietary Names for Pharmaceutical Substances (INN) WHO Drug Information (Dec. 18, 2015) vol. 29, No. 4, pp. 503 and 506.
Amendment No. 2 to Form S-1 Registration Statement Securities and Exchange Commission describing ChemoCentryx, Inc.'s efforts with CCX 168 and ongoing Phase II study for treatment of AAV (filed Jan. 6, 2012); 211 pages. [https://www.sec.gov/Archives/edgar/data/1340652/000119312512005295/d237820ds1a.htm].
Bekker, Pirow et al., "Characterization of Pharmacologic and Pharmacokinetic Properties of CCX168, a Potent and Selective Orally Administered Complement 5a Receptor Inhibitor, Based on Preclinical Evaluation and Randomized Phase 1 Clinical Study," *PLOS One* [DOI: 10.1371/journal.pone.0164646 (Oct. 21, 2016); 19 pages.

(Continued)

*Primary Examiner* — Sikarl A Witherspoon
(74) *Attorney, Agent, or Firm* — Robert Bernstein

(57) ABSTRACT

The present disclosure provides methods for treating ANCA-associate vasculitis in a human in need thereof, the method comprising administering to the human a therapeutically effective amount of avacopan:

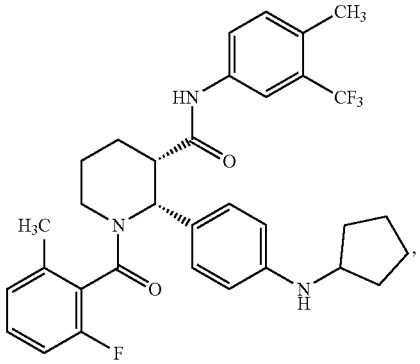

or a pharmaceutically acceptable salt thereof, such that the level of plasma complement factor Bb, C3a, or C5a does not significantly change in the human upon treatment.

24 Claims, 18 Drawing Sheets

(56) References Cited

OTHER PUBLICATIONS

"A Study to Evaluate the Safety and Efficacy of CCX168 in Subjects with ANCA-Associated Vasculitis," Clinical Trials.gov Identifier NCT01363388; CCX168 AAV Study Description Trial record 5 of 11 for Completed Studies / ChemoCentryx (First Posted Jun. 1, 2011); 6 pages. [https://clinicaltrials.gov/ct2/show/NCT01363388?recrs=e&spons=chemocentryx&draw=2&rank=5].
"Clinical Trial to Evaluate Safety and Efficacy of CCX168 in ANCA-Associated Vasculitis," Clinical Trials.gov Identifier NCT02222155; CCX168 AAV Study Description Trial record 2 of 11 for Completed Studies / ChemoCentryx (First Posted Aug. 21, 2014); 6 pages.
Deng, Jun, et al., "Rapid reduction in urinary SCD!63 correlates with clinical benefit in the clear study of C5AR inhibitor avacopan in ANCA-associated vasculitis," *American Society of Nephrology Kidney Week 2017* (Oct. 31, 2017) Abstract only; 3 pages.
Etzerodt, Anders et al., "CD163 and Inflammation: Biological, Diagnostic, and Therapeutic Aspects," *Antioxidants & Redox Signaling* (2013; acceptance date Aug. 19, 2012) 18(17):2352-2363.
Free, Meghan E. et al., "The Search for a Biomarker of Relapse in ANCA-Associated Vasculitis," *Journal of the American Society of Nephrology* (Sep. 1, 2016) 27(9):2551-2553.
Groselj-Grenc, Mojca et al., "Neutrophil and Monocyte CD64 and CD163 Expression in Critically Ill Neonates and Children with Sepsis: Comparison of Flurescence Intensities and Calculated Indexes," Hindawi Publishing Corporation; *Mediators of Inflammation*, vol. 2008 (accepted Apr. 23, 2008), Article ID 202646; 10 pages.
Jain, U. et al., "The C5a receptor antagonist PMX205 ameliorates experimentally induced colitis associated with increased IL-4 and IL-10," *British Journal of Pharmacology* (2013; accepted Aug. 10, 2012); 168:488-501.
Jayne, David R. W. et al., "Randomized Trial of C5a Receptor Inhibitor Avacopan in ANCA-Associated Vasculitis," *Journal of the American Society of Nephrology* (Sep. 2017; Epub Apr. 11, 2017); 28(9):1-9 (pp. 2756-2767).
Li, Ke et al., "The relative importance of local and systemic complement production in ischaemia, transplantation and other pathologies," *Molecular Immunology* (2007; Rec'd May 31, 2007) 44:3866-3874.
Moreno, Juan Antonio et al., "In vitro and in vivo evidence for the role of elastase shedding of CD163 in human atherothrombosis," *European Heart Journal* (2012; online published May 23, 2011); 33:252-263.
Nagai, M. et al., "Serum levels of the soluble haemoglobin scavenger receptor CD163 in MPO-ANCA-associated renal vasculitis," *Scandinavian Journal of Rheumatology* (Apr. 20, 2016) 45:397-403 (Abstract only).
O'Reilly, Vincent P. et al., "Urinary Soluble CD163 in Active Renal Vasculitis," *Journal of the American Society of Nephrology* (Aug. 31, 2016); 27:2906-2916.
Press Release: ChemoCentryx Announces Presentation of Positive Results from Phase II ANCA-Associated Vasculitis Clear Trial of Orally Administered Complement 5a Receptor Inhibitor CCX168 at the $53^{rd}$ ERA-EDTA Congress (May 23, 2016); 5 pages.
Press Release "ChemoCentryx Announces Positive Results in Phase II ANCA-Associated Vasculitis Clear Trial of Orally Administered Complement 5a Receptor Inhibitor CCX168," (Jan. 6, 2016); four pages.
Pubmed Compound Summary for CID 49841217, Avacopan, U.S. National Library of Medicine (Jan. 24, 2011), pp. 1-22 (p. 3) (https://pubchem.ncbi.nlm.nih.gov/compound/49841217).
Rousselle, Anthony et al., "Monocytes Promote Crescent Formation in Anti-Myeloperoxidase Antibody—Induced Glomerulonephritis," *The American Journal of Pathology* (Sep. 2017; accepted for publication May 2, 2017) 187(9):1908-1915.
Wong, Linda et al., "Monochromatic Gating Method by Flow Cytometry for High Purity Monocyte Analysis," *Cytometry Part B (Clinical Cytometry)* (published online Jan. 2, 2013) 84B:119-124.
Xiao et al., "C5a Receptor (CD88) Blockade Protects against MPO-ANCA GN," *J. Am. Soc. Nephrol.* (2014; accepted for publication Aug. 5, 2013); 25(2):225-231.
Yuen, Joshua et al., "NETosing Neutrophils Activate Complement Both on Their Own NETs and Bacteria via Alternative and Non-alternative Pathways," *Frontiers in Immunology* (Apr. 14, 2016) 7(137):1-14.
Zhao, Lei et al., "M2 Macrophage Infiltrates in the Early Stages of ANCA-Associated Pauci-Immune Necrotizing GN," *Clin J Am Soc Nephrol* (Jan. 2015; accepted Sep. 8, 2014) 10:54-62.

DOSING AND EFFECT OF C5a ANTAGONIST WITH ANCA-ASSOCIATED VASCULITIS

CROSS-REFERENCES TO RELATED APPLICATIONS

This application is an application claiming benefit under 35 U.S.C. § 119(e) of U.S. Provisional Application No. 62/682,013 filed Jun. 7, 2018, which is incorporated herein by reference in its entirety.

STATEMENT AS TO RIGHTS TO INVENTIONS MADE UNDER FEDERALLY SPONSORED RESEARCH AND DEVELOPMENT

NOT APPLICABLE

REFERENCE TO A "SEQUENCE LISTING," A TABLE, OR A COMPUTER PROGRAM LISTING APPENDIX SUBMITTED ON A COMPACT DISK

NOT APPLICABLE

BACKGROUND OF THE INVENTION

Anti-neutrophil cytoplasmic antibodies (ANCA) are a group of autoantibodies of the IgG type that react with the cytoplasmic constituents of neutrophils and monocytes. The interaction between primed neutrophils and ANCAs releases factors that activate the alternative complement pathway, initiating an amplification loop that is thought to sustain necrotizing inflammation during flares of ANCA-associated vasculitis (AAV).

A number of drug candidates targeting various components of the complement pathway are in development. However, many of the drugs in development have undesirable adverse effects. For example, eculizumab, an antibody that binds to the complement component C5 and inhibits the formation of C5a and C5b, blocks downstream formation of the membrane attack complex. This negatively affects an individual's ability to fight infections and has prompted the FDA to require a black box warning for eculizumab.

Thus, there is a need in the art to develop drugs that effectively ameliorate the effects of AAV, but do not significantly alter the complement pathway.

BRIEF SUMMARY

The present disclosure is directed to, inter alia, methods of treating ANCA-associated vasculitis (AAV) in a human in need thereof, the method comprising administering to the human a therapeutically effective amount of avacopan, having the structure shown below:

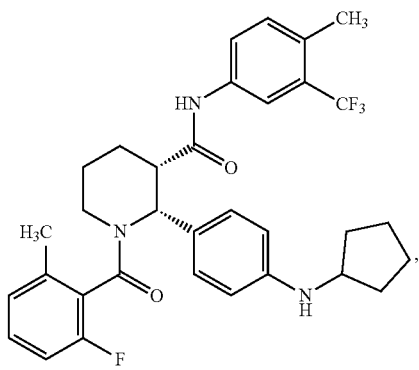 [SMILES: Cc1ccc(NC(=O)[C@H]2CCCN(C(=O)c3c(C)cccc3F)[C@H]2c2ccc(NC3CCCC3)cc2)cc1C(F)(F)F]

or a pharmaceutically acceptable salt thereof,
such that the level of plasma complement factor Bb, C3a, or C5a does not significantly change in the human upon treatment.

Other objects, features, and advantages of the present invention will be apparent to one of skill in the art from the following detailed description and figures.

DETAILED DESCRIPTION OF THE INVENTION

I. General

Figure 1:
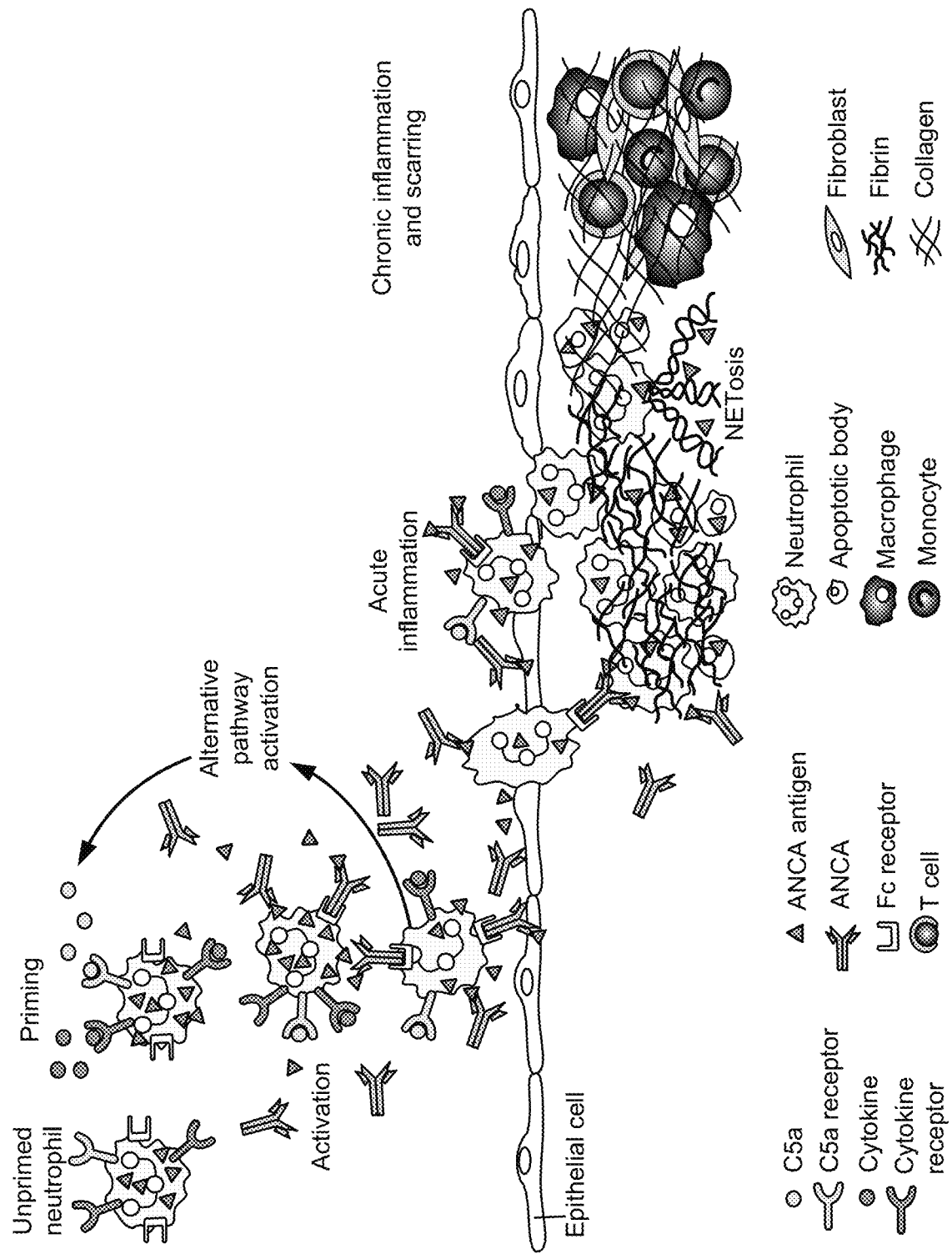
FIG. 1 provides a schematic with a model describing the pathogenesis of ANCA-Associated Vasculitis demonstrating that c5a and c5aR drive ANCA-associated vasculitis.
Figure 2:
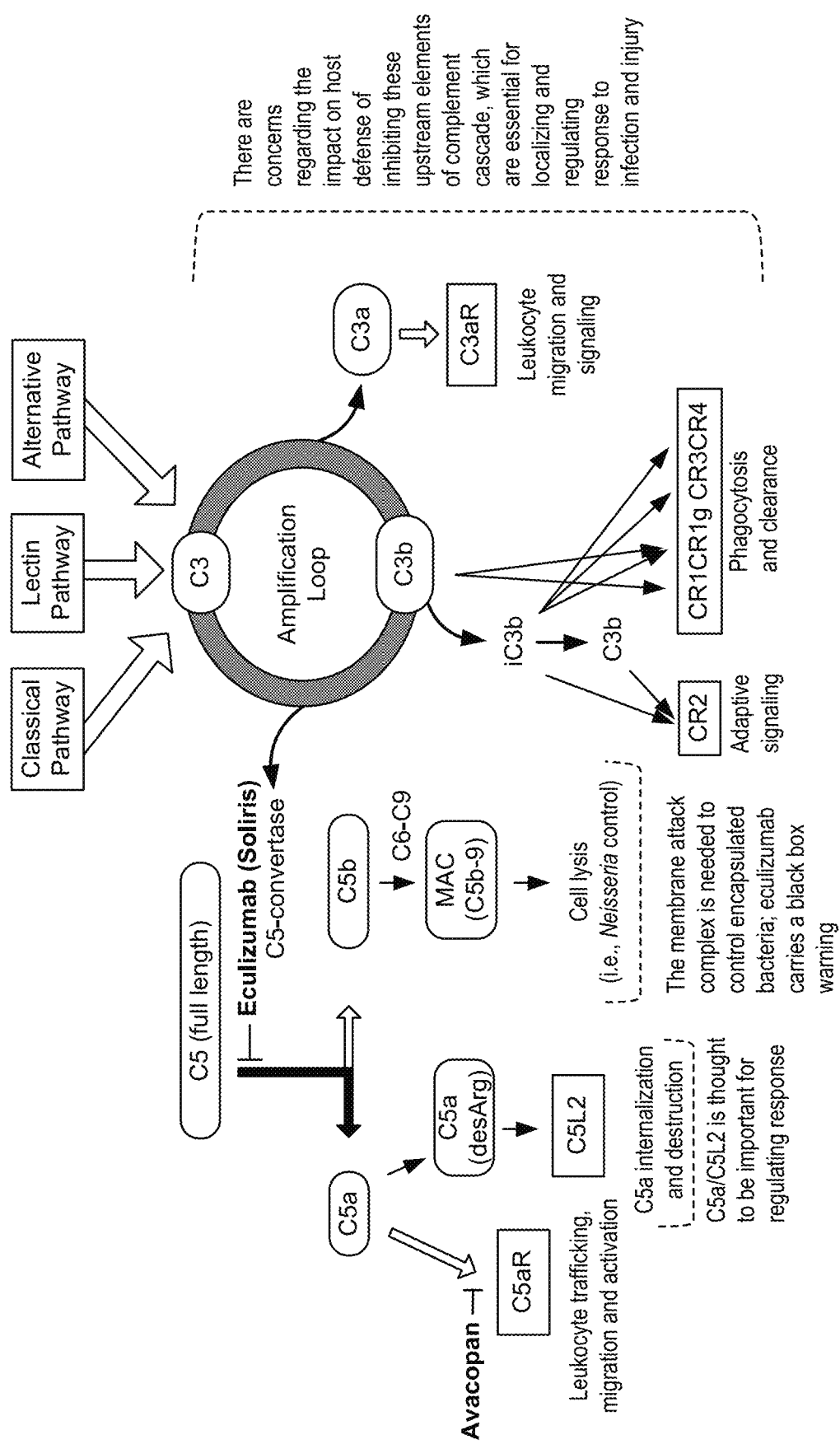
FIG. 2 provides a schematic illustrating that Avacopan targets the distal complement pathway.
Figure 3A:
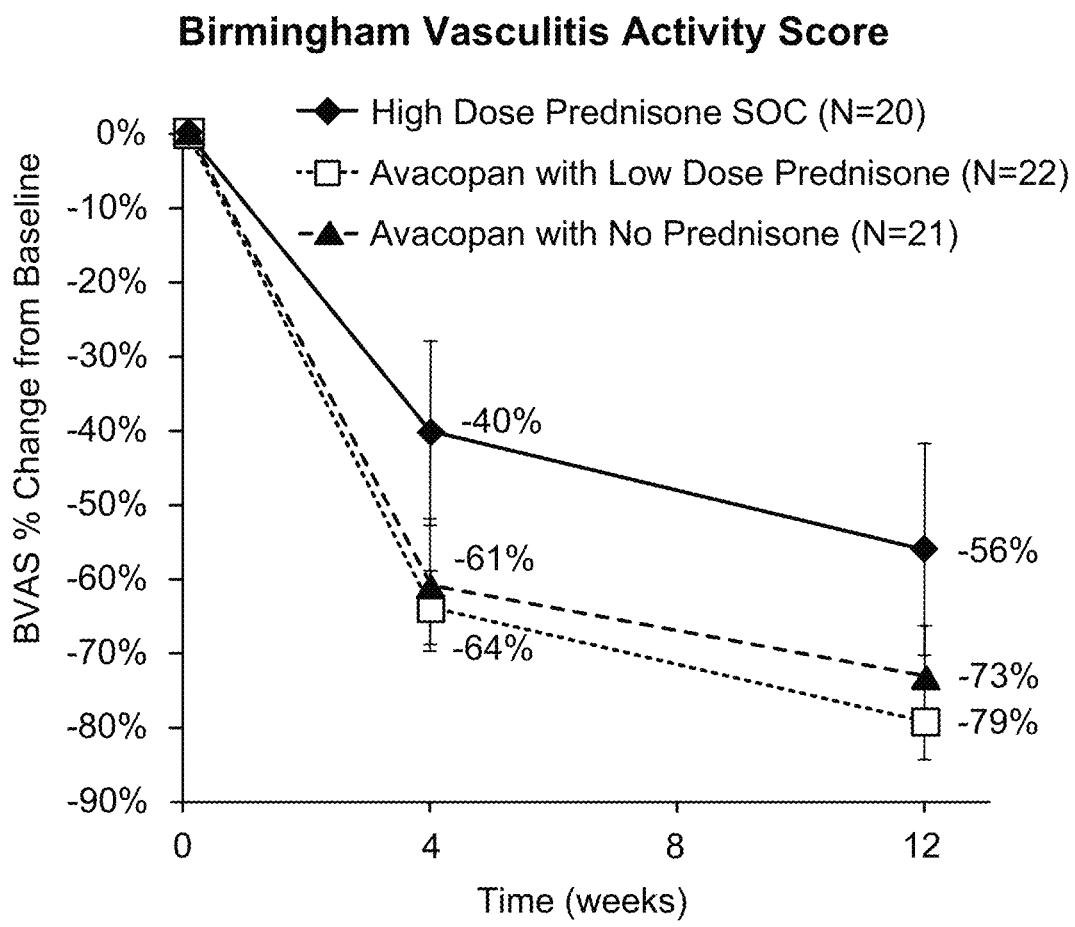
FIG. 3A-E illustrates results obtain from the CLEAR trial, which demonstrated a rapid decrease in disease activity and significant improvement in health-related quality of life in patients treated with avacopan. (A) plots the Birmingham Vasculitis Activity Score; (B) plots the urinary albumin to creatine ration; (C) plots the EuroQOL-5D-5L visual analogue scale; (D) plots the Short Form-36 physical functioning results; and (E) plots the Short Form-36 role emotional results. Patients receiving high dose prednisone are plotted with diamonds; patients receiving avacopan with low dose prednisone are plotted with squares; and patients receiving avacopan with no prednisone are plotted with triangles.
Figure 3B:
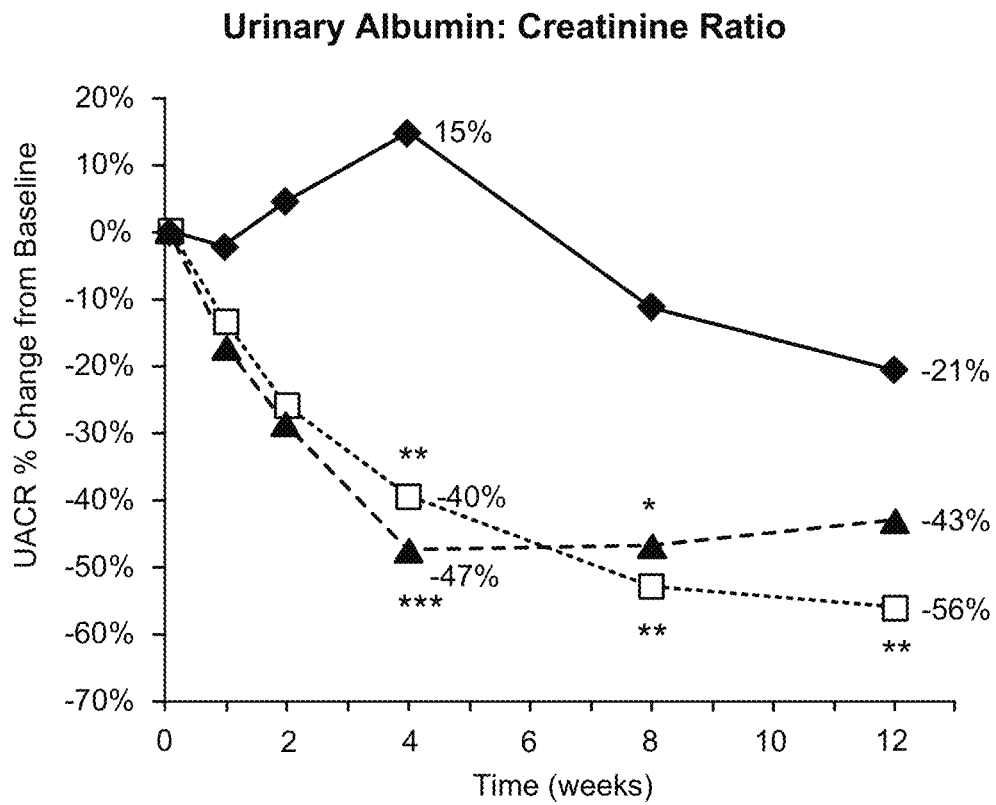
Figure 3C:
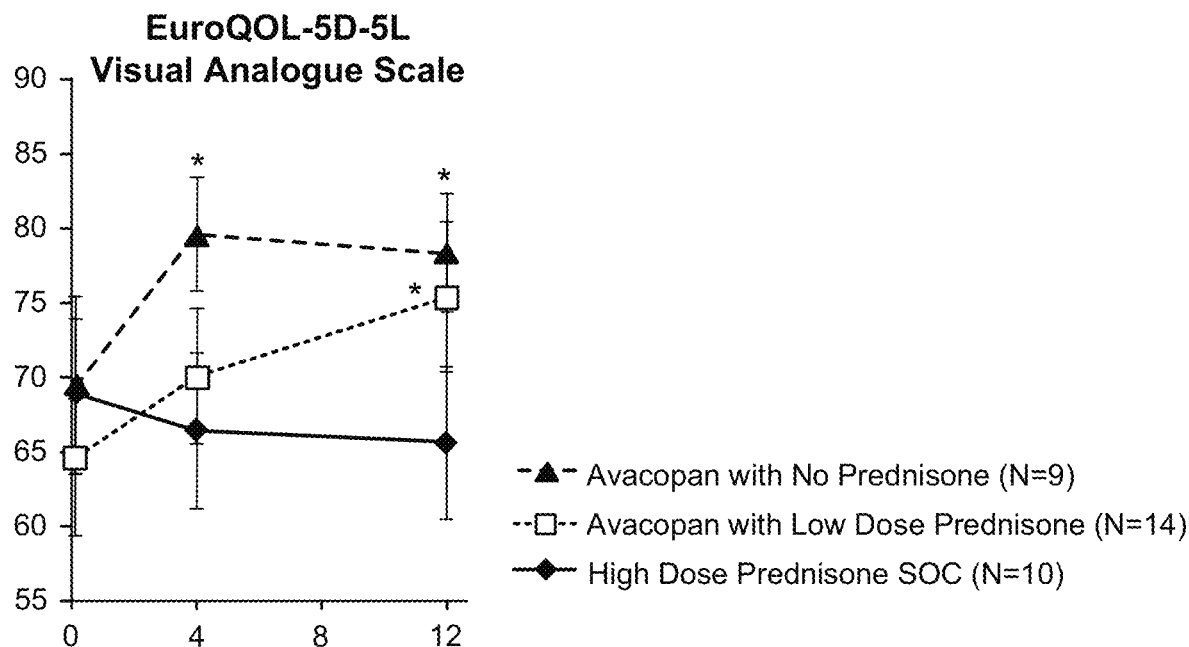
Figure 3D:
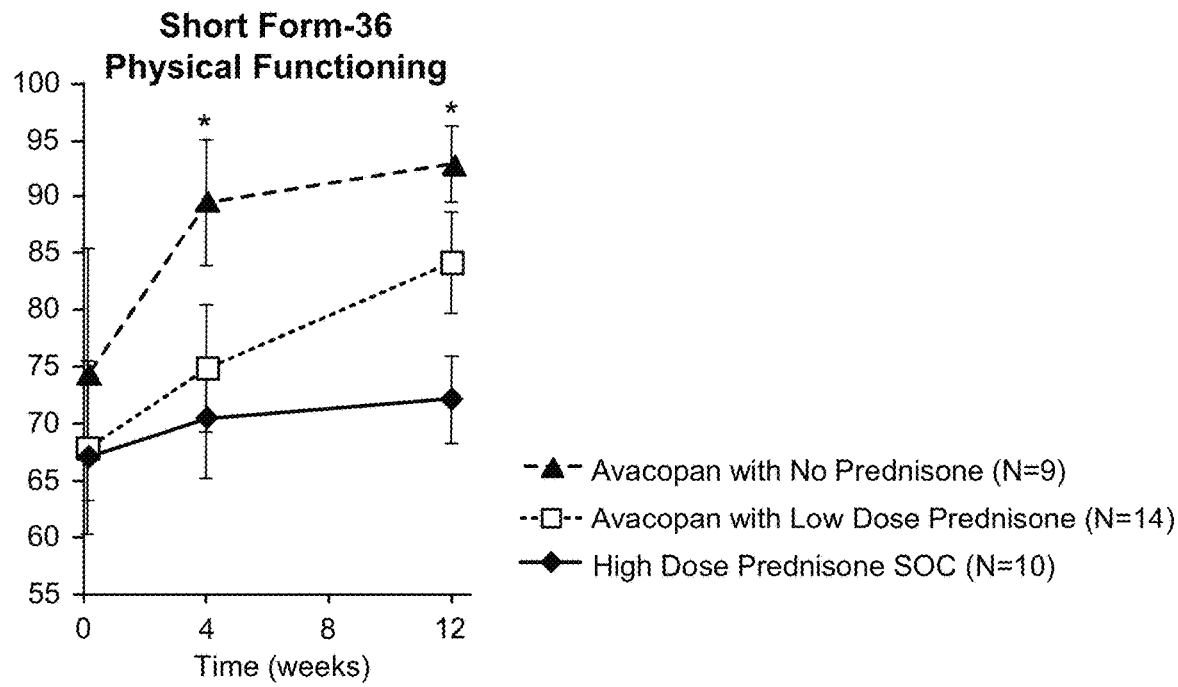
Figure 3E:
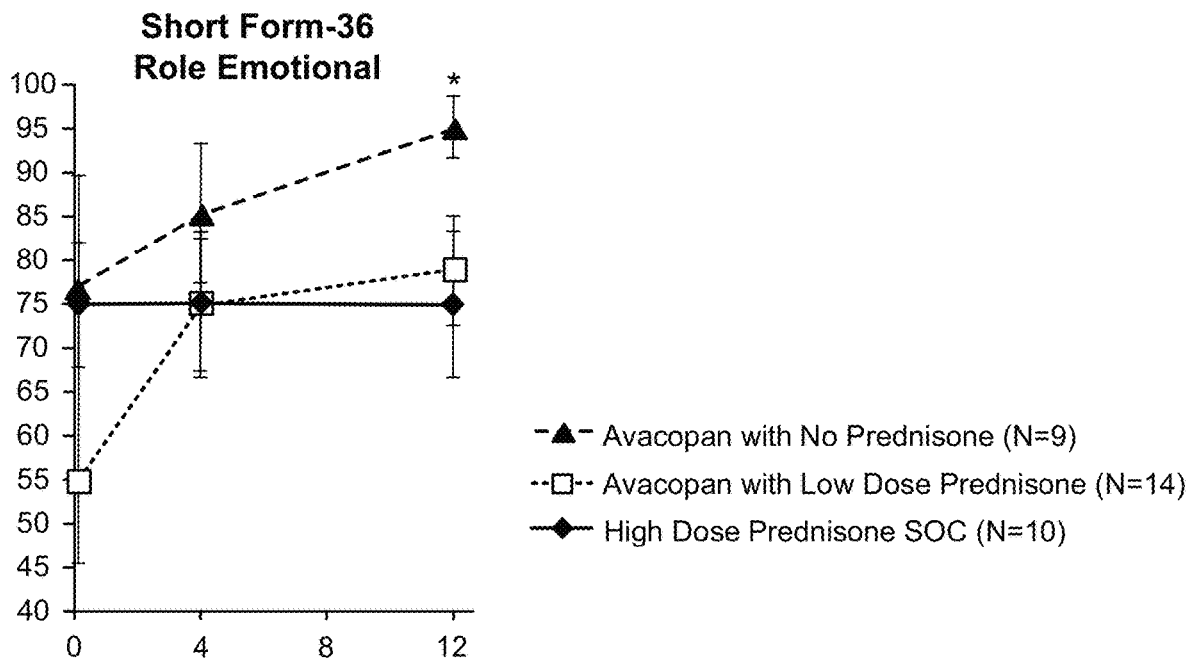
Figure 4A:
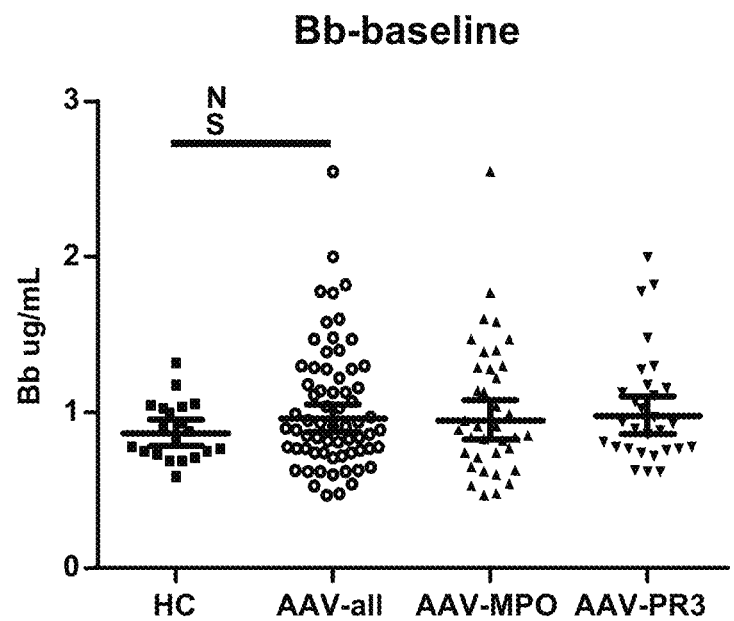
FIG. 4A-E plots the baseline levels of Bb (A), C3a (B), C5a (C), sC5b-9 (D) and properdin (E) in healthy control patients (HC), all AAV patients (AAV-all), patients with anti-MPO AAV (AAV-MPO), and patients with anti-PR3 AAV (AAV-PR3). No difference between baseline complement levels in anti-MPO and anti-PR3 positive patients.
Figure 4B:
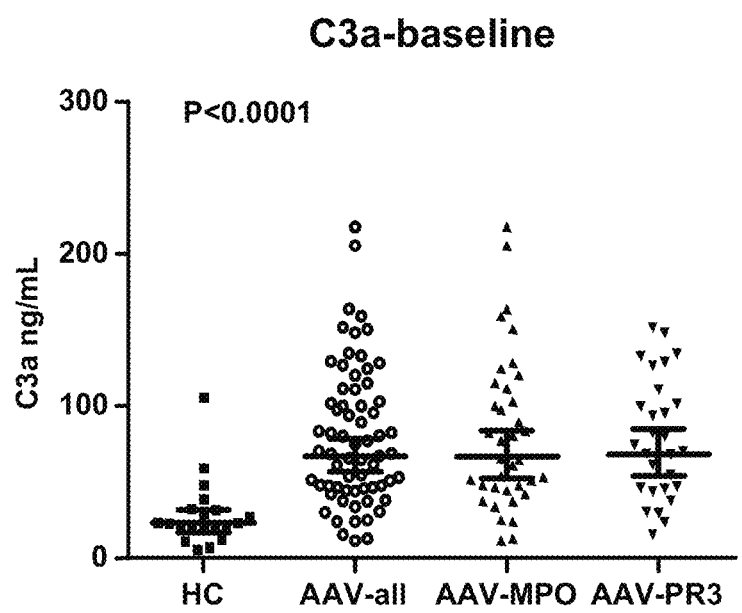
Figure 4C:
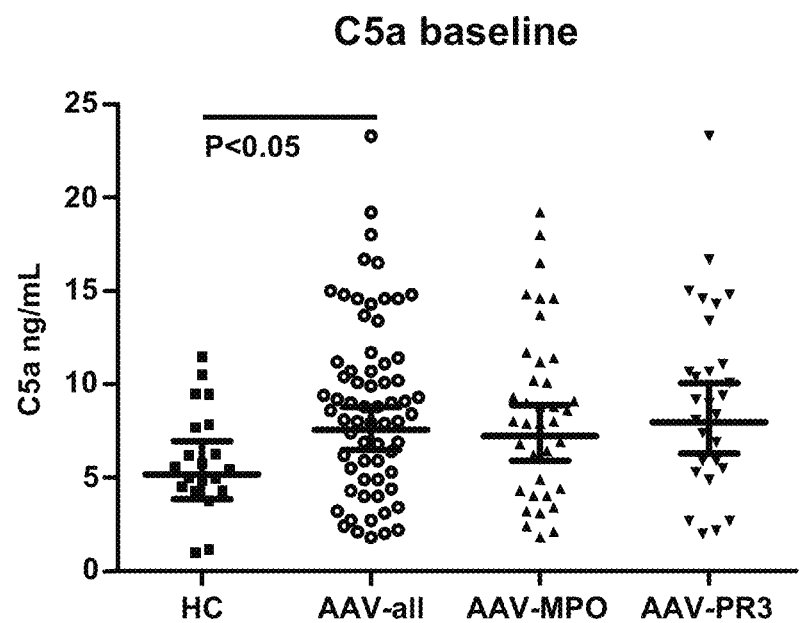
Figure 4D:
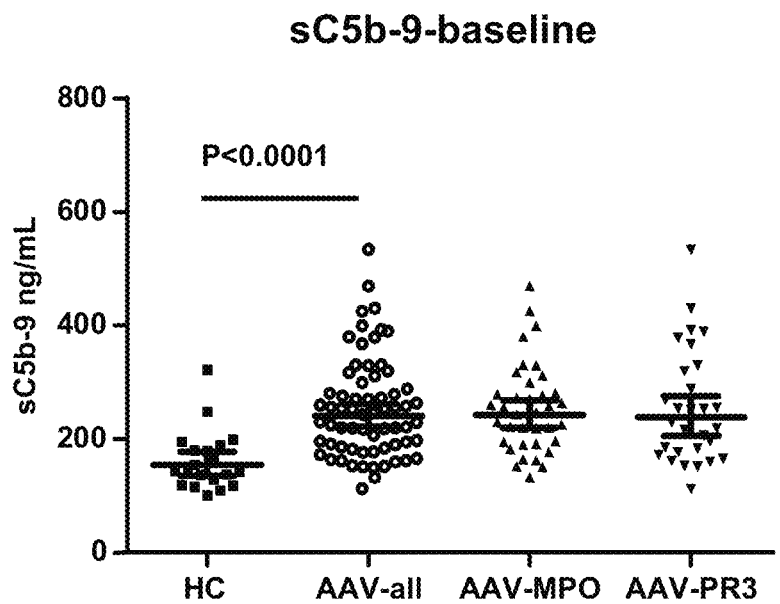
Figure 4E:
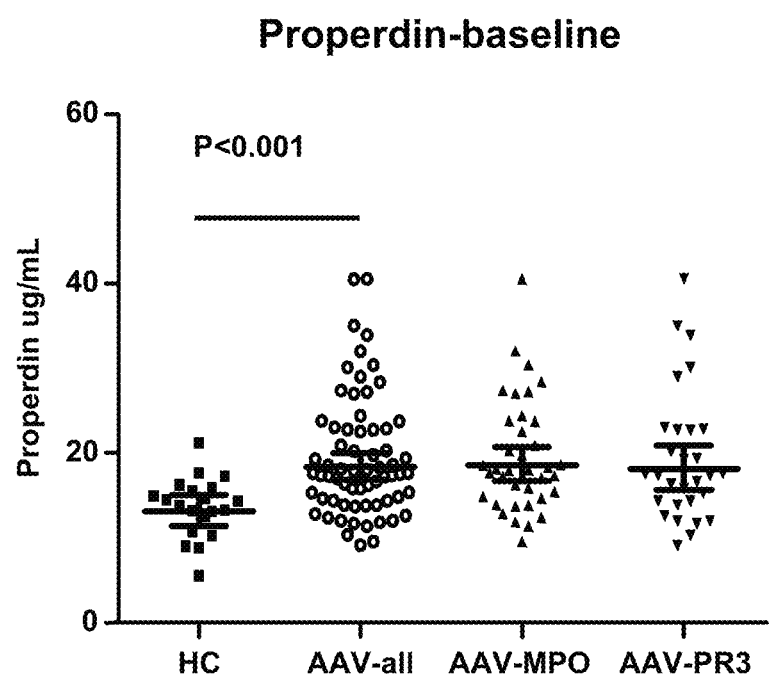

The present disclosure demonstrates the surprising and unexpected finding that avacopan rapidly improves AAV without impacting the level of plasma complement factors in individuals receiving treatment. Thus, individuals receiving avacopan do not experience a significant change in the level of plasma complement factors such as Bb, C3a or C5a and, advantageously, assembly of the membrane attack complex or upstream complement activities is not impacted.

II. Definitions

Unless specifically indicated otherwise, all technical and scientific terms used herein have the same meaning as commonly understood by those of ordinary skill in the art to which this invention belongs. In addition, any method or material similar or equivalent to a method or material described herein can be used in the practice of the present invention. For purposes of the present invention, the following terms are defined.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention. Unless defined otherwise, all technical and scientific terms used herein have the same meaning as commonly understood by one of ordinary skill in the art to which this invention belongs.

The terms "a," "an," or "the" as used herein not only include aspects with one member, but also include aspects with more than one member. For instance, the singular forms "a," "an," and "the" include plural referents unless the context clearly dictates otherwise. Thus, for example, reference to "a cell" includes a plurality of such cells and reference to "the agent" includes reference to one or more agents known to those skilled in the art, and so forth.

As used herein, the term "treating" or "treatment" encompasses both disease-modifying treatment and symptomatic treatment, either of which may be prophylactic (i.e., before the onset of symptoms, in order to prevent, delay or reduce the severity of symptoms) or therapeutic (i.e., after the onset of symptoms, in order to reduce the severity and/or duration of symptoms).

The term "pharmaceutically acceptable salts" is meant to include salts of the active compounds which are prepared with relatively nontoxic acids or bases, depending on the particular substituents found on the compounds described herein. When compounds of the present disclosure contain relatively acidic functionalities, base addition salts can be obtained by contacting the neutral form of such compounds with a sufficient amount of the desired base, either neat or in a suitable inert solvent. Examples of salts derived from pharmaceutically-acceptable inorganic bases include aluminum, ammonium, calcium, copper, ferric, ferrous, lithium, magnesium, manganic, manganous, potassium, sodium, zinc and the like. Salts derived from pharmaceutically-acceptable organic bases include salts of primary, secondary and tertiary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperadine, polyamine resins, procaine, purines, theobromine, triethylamine, trimethylamine, tripropylamine, tromethamine and the like. When compounds of the present disclosure contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galacturonic acids and the like (see, for example, Berge, S. M., et al, "Pharmaceutical Salts", *Journal of Pharmaceutical Science*, 1977, 66, 1-19). Certain specific compounds of the present disclosure contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present disclosure.

The compound described in the Embodiments below can be obtained according to methods described in WO 2010/075257, WO 2011/163640 and WO 2016/053890.

III. Detailed Description of the Embodiments

Methods of Treatment

In some aspects provided herein are methods of treating ANCA-associated vasculitis in a human in need thereof, the method comprising administering to the human a therapeutically effective amount of avacopan:

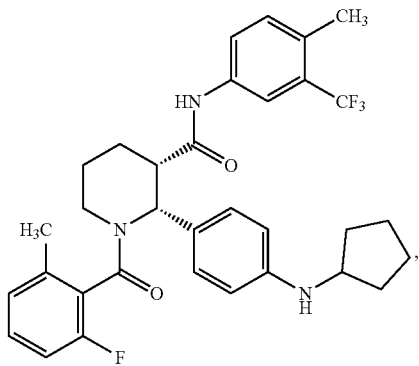 [SMILES: Cc1ccc(NC(=O)[C@H]2CCCN(C(=O)c3c(C)cccc3F)[C@H]2c2ccc(NC3CCCC3)cc2)cc1C(F)(F)F]

or a pharmaceutically acceptable salt thereof,
such that the level of plasma complement factor Bb, C3a, or C5a does not significantly change in the human upon treatment.

Avacopan can be administered in using a variety of different administration routes. In some embodiments, the methods include orally administering avacopan or a pharmaceutically acceptable salt thereof. In some embodiments, the methods include intravenously administering avacopan or a pharmaceutically acceptable salt thereof.

Patients receiving avacopan are administered a dosage amount that provides a therapeutic benefit. In some embodiments, dosage amounts that provide a therapeutic benefit include, but are not limited to, a dosage of about of 10 mg, 15 mg, 20 mg, 25 mg, 30 mg, 35 mg, 40 mg, 45 mg, 50 mg, 55 mg, 60 mg, 65 mg, or 70 mg. In some embodiments, the methods include administering about 30 mg avacopan.

The frequency of dosing depends on a variety of factors including the dosage amount of avacopan administered to patients receiving treatment as well as the stage of disease being treated. In some embodiments, the methods include administering the avacopan twice daily. In some embodiments, the methods include administering the avacopan once daily. In some embodiments, the total daily dosage of avacopan is about 40 mg, 50 mg, 60 mg or 70 mg. In some embodiments, the total daily dosage of avacopan is about 60 mg.

The duration of treatment will depend on a number of factors including the daily amount administered, the stage of disease being treated, and response of the patient. In some embodiments, the methods include administering the avacopan for at least 4 weeks, 8 weeks, 12 weeks, 16 weeks, 20 weeks, 24 weeks, 28 weeks, 32 weeks, 36 weeks, or 40 or more weeks. In some embodiments, the methods include administering avacopan for at least 12 weeks. In some embodiments, the methods include administering avacopan chronically.

In some embodiments, the level of complement factor Bb does not significantly change. In some embodiments, the levels of complement factor Bb are compared immediately before the treatment and after at least a week or about a month of treatment. In some embodiments, the level of complement factor Bb after the treatment is within about 30%, about 20%, or about 10% of the level before the treatment.

In some embodiments, the level of complement factor Bb before and after the treatment are from about 0.8 to 1.4 µg/mL. In some embodiments, the level of complement factor Bb before and after the treatment are from about 0.4 to 2 µg/mL. In some embodiments, the level of complement factor Bb before and after the treatment are from about 0.4 to 1.4 µg/mL. In some embodiments, the level of complement factor Bb before and after the treatment are from about 0.4 to 1.2 µg/mL. In some embodiments, the level of complement factor Bb before and after the treatment are from about 0.4 to 1.0 µg/mL. In some embodiments, the level of complement factor Bb before and after the treatment are from about 0.4 to 0.8 µg/mL. In some embodiments, the level of complement factor Bb before and after the treatment are from about 0.6 to 1.2 µg/mL. In some embodiments, the level of complement factor Bb before and after the treatment are from about 0.8 to 1.2 µg/mL. In some embodiments, the level of complement factor Bb before and after the treatment are from about 1.0 to 1.6 µg/mL. In some embodiments, the level of complement factor Bb before and after the treatment are from about 1.0 to 1.4 µg/mL.

In some embodiments, the levels of complement factor C3a does not significantly change. In some embodiments, the levels of complement factor C3a are compared immediately before the treatment and from about 1 to about 6 hours after start of the treatment. In some embodiments, the levels of complement factor C3a are compared immediately before the treatment and after at least a week or about a month of treatment. In some embodiments, the level of complement factor C3a after the treatment is within about 30%, about 20%, or about 10% of the level before the treatment.

In some embodiments, the level of complement factor C3a before and after the treatment are from about 25 to 100 ng/mL. In some embodiments, the level of complement factor C3a before and after the treatment are from about 10 to 180 ng/mL. In some embodiments, the level of complement factor C3a before and after the treatment are from about 15 to 85 ng/mL. In some embodiments, the level of complement factor C3a before and after the treatment are from about 25 to 75 ng/mL. In some embodiments, the level of complement factor C3a before and after the treatment are from about 30 to 75 ng/mL. In some embodiments, the level of complement factor C3a before and after the treatment are from about 50 to 180 ng/mL. In some embodiments, the level of complement factor C3a before and after the treatment are from about 60 to 120 ng/mL. In some embodiments, the level of complement factor C3a before and after the treatment are from about 50 to 150 ng/mL.

In some embodiments, the levels of complement factor C5a does not significantly change. In some embodiments, the levels of complement factor C5a are compared immediately before the treatment and after at least a week or about a month of treatment. In some embodiments, the level of complement factor C5a after the treatment is within about 30%, about 20%, or about 10% of the level before the treatment.

In some embodiments, the level of complement factor C5a before and after the treatment are from about 4 to 10 ng/mL. In some embodiments, the level of complement factor C5a before and after the treatment are from about 2 to 20 ng/mL. In some embodiments, the level of complement factor C5a before and after the treatment are from about 3 to 15 ng/mL. In some embodiments, the level of complement factor C5a before and after the treatment are from about 3 to 8 ng/mL. In some embodiments, the level of complement factor C5a before and after the treatment are from about 6 to 15 ng/mL. In some embodiments, the level of complement factor C5a before and after the treatment are from about 5.5 to 12.5 ng/mL. In some embodiments, the level of complement factor C5a before and after the treatment are from about 7 to 10 ng/mL.

ANCA-associate vasculitis can be caused by the formation of autoantibodies targeting various antigens. In some embodiments, the ANCA-associated vasculitis is caused by anti-MPO antibodies. In some embodiments, the ANCA-associated vasculitis is caused by anti-PR3 antibodies.

In some aspects provided herein are methods of inhibiting C5aR in a human in need thereof, comprising administering to the human a therapeutically effective amount of avacopan:

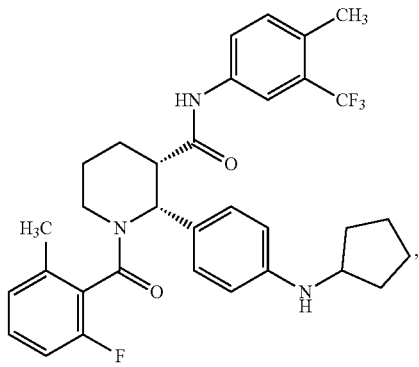 [SMILES: Cc1ccc(NC(=O)[C@H]2CCCN(C(=O)c3c(C)cccc3F)[C@H]2c2ccc(NC3CCCC3)cc2)cc1C(F)(F)F]

or a pharmaceutically acceptable salt thereof,
such that the level of plasma complement factor Bb, C3a, or C5a does not significantly change in the human upon C5aR inhibition.

Avacopan can be administered in using a variety of different administration routes. In some embodiments, the methods include orally administering avacopan or a pharmaceutically acceptable salt thereof. In some embodiments, the methods include intravenously administering avacopan or a pharmaceutically acceptable salt thereof.

Patients receiving avacopan are administered a dosage amount that provides a therapeutic benefit. In some embodiments, dosage amounts that provide a therapeutic benefit include, but are not limited to, a dosage of about of 10 mg, 15 mg, 20 mg, 25 mg, 30 mg, 35 mg, 40 mg, 45 mg, 50 mg, 55 mg, 60 mg, 65 mg, or 70 mg. In some embodiments, the methods include administering about 30 mg avacopan.

The frequency of dosing depends on a variety of factors including the dosage amount of avacopan administered to patients receiving treatment as well as the stage of disease being treated. In some embodiments, the methods include administering the avacopan twice daily. In some embodiments, the methods include administering the avacopan once daily. In some embodiments, the total daily dosage of avacopan is about 40 mg, 50 mg, 60 mg or 70 mg. In some embodiments, the total daily dosage of avacopan is about 60 mg.

The duration of treatment will depend on a number of factors including the daily amount administered, the stage of disease being treated, and response of the patient. In some embodiments, the methods include administering avacopan for at least 4 weeks, 8 weeks, 12 weeks, 16 weeks, 20 weeks, 24 weeks, 28 weeks, 32 weeks, 36 weeks, or 40 or more weeks. In some embodiments, the methods include administering avacopan for at least 12 weeks. In some embodiments, the methods include administering avacopan chronically.

In some embodiments, the level of the complement factor after the administration is within about 30%, about 20%, or about 10% of the level before the administration.

Combination therapy is also contemplated in the current disclosure. In some embodiments, the methods described herein further include administering a corticosteroid. In some embodiments, the corticosteroid is prednisone, bethamethasone, prednisolone, triamcinolone, methylprednisolone, dexamethasone, or fludrocortisone. In some embodiments, the corticosteroid is prednisone. In some embodiments, the methods described herein further include administering a CD20 inhibitor. In some embodiments, the CD20 inhibitor is rituximab, ofatumumab, ocrelizumab, tositumomab, obinutuzumab, or ibritumomab. In some embodiments, the CD20 inhibitor is rituximab. In some embodiments, the methods described herein further include administering cyclophosphamide.

Pharmaceutical Compositions

Avacopan can be administered as a composition which will typically contain a pharmaceutical carrier or diluent.

The term "composition" as used herein is intended to encompass a product comprising the specified ingredients in the specified amounts, as well as any product which results, directly or indirectly, from combination of the specified ingredients in the specified amounts.

In some embodiments, the pharmaceutical composition further comprises one or more additional therapeutic agents.

The pharmaceutical compositions for the administration of the compounds of this disclosure may conveniently be presented in unit dosage form and may be prepared by any of the methods well known in the art of pharmacy and drug delivery. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases.

The pharmaceutical compositions containing the active ingredient may be in a form suitable for oral use, for example, as tablets, troches, lozenges, aqueous or oily suspensions, dispersible powders or granules, emulsions and self-emulsifications as described in U.S. Patent Application 2002-0012680, hard or soft capsules, syrups, elixirs, solutions, buccal patch, oral gel, chewing gum, chewable tablets, effervescent powder and effervescent tablets. Compositions intended for oral use may be prepared according to any method known to the art for the manufacture of pharmaceutical compositions and such compositions may contain one or more agents selected from the group consisting of sweetening agents, flavoring agents, coloring agents, antioxidants and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as cellulose, silicon dioxide, aluminum oxide, calcium carbonate, sodium carbonate, glucose, mannitol, sorbitol, lactose, calcium phosphate or sodium phosphate; granulating and disintegrating agents, for example, corn starch, or alginic acid; binding agents, for example PVP, cellulose, PEG, starch, gelatin or acacia, and lubricating agents, for example magnesium stearate, stearic acid or talc. The tablets may be uncoated or they may be coated, enterically or otherwise, by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for controlled release.

Formulations for oral use may also be presented as hard gelatin capsules wherein the active ingredient is mixed with an inert solid diluent, for example, calcium carbonate, calcium phosphate or kaolin, polyethylene glycol (PEG) of various average sizes (e.g., PEG400, PEG4000) and certain surfactants such as cremophor or solutol, or as soft gelatin capsules wherein the active ingredient is mixed with water or an oil medium, for example peanut oil, liquid paraffin, or olive oil. Additionally, emulsions can be prepared with a non-water miscible ingredient such as oils and stabilized with surfactants such as mono- or di-glycerides, PEG esters and the like.

Aqueous suspensions that contain the active materials in admixture (with excipients suitable for the manufacture of aqueous suspensions) are also suitable in the present methods. Such excipients are suspending agents, for example sodium carboxymethylcellulose, methylcellulose, hydroxypropylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxy-ethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the disclosure may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. Oral solutions can be prepared in combination with, for example, cyclodextrin, PEG and surfactants.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compound (avacopan), or a composition thereof, may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include cocoa butter and polyethylene glycols. Additionally, the compounds can be administered via ocular delivery by means of solutions or ointments. Still further, transdermal delivery of the subject compounds can be accomplished by means of iontophoretic patches and the like. For topical use, creams, ointments, jellies, solutions or suspensions, etc., containing the compounds of the present disclosure are employed. As used herein, topical application is also meant to include the use of mouth washes and gargles.

The compound (avacopan), or a composition thereof, may also be coupled a carrier that is a suitable polymers as targetable drug carriers. Such polymers can include polyvinylpyrrolidone, pyran copolymer, polyhydroxy-propylmethacrylamide-phenol, polyhydroxyethyl-aspartamide-phenol, or polyethyleneoxide-polylysine substituted with palmitoyl residues. Furthermore, the compounds of the disclosure may be coupled to a carrier that is a class of biodegradable polymers useful in achieving controlled release of a drug, for example polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross linked or amphipathic block copolymers of hydrogels. Polymers and semipermeable polymer matrices may be formed into shaped articles, such as valves, stents, tubing, prostheses and the like. In one embodiment of the disclosure, the compound of the disclosure is coupled to a polymer or semipermeable polymer matrix that is formed as a stent or stent-graft device.

IV. Particular Embodiments

Embodiment 1: A method of treating ANCA-associated vasculitis in a human in need thereof, the method comprising administering to the human a therapeutically effective amount of avacopan:

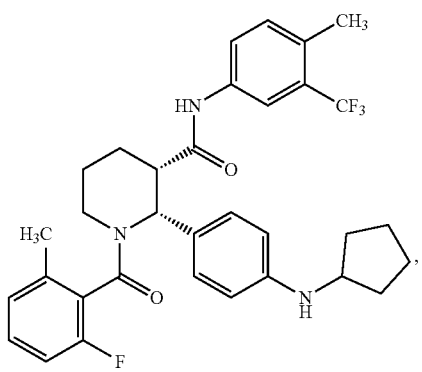 [SMILES: Cc1ccc(NC(=O)[C@H]2CCCN(C(=O)c3c(C)cccc3F)[C@H]2c2ccc(NC3CCCC3)cc2)cc1C(F)(F)F]

or a pharmaceutically acceptable salt thereof,
such that the level of plasma complement factor Bb, C3a, or C5a does not significantly change in the human upon treatment.

Embodiment 2: The method of embodiment 1, comprising orally administering the avacopan or pharmaceutically acceptable salt thereof.

Embodiment 3: The method of embodiment 1 or 2, comprising administering avacopan.

Embodiment 4: The method of any one of embodiments 1 to 3, comprising administering about 30 mg avacopan.

Embodiment 5: The method of any one of embodiments 1 to 4, comprising administering the avacopan twice daily.

Embodiment 6: The method of any one of embodiments 1 to 5, comprising administering the avacopan for at least 12 weeks.

Embodiment 7: The method of any one of embodiments 1 to 6, wherein the level of complement factor Bb does not significantly change.

Embodiment 8: The method of embodiment 7, wherein the levels of complement factor Bb are compared immediately before the treatment and after at least a week or about a month of treatment.

Embodiment 9: The method of any one of embodiments 1 to 8, wherein the levels of complement factor C3a does not significantly change.

Embodiment 10: The method of embodiment 9, wherein the levels of complement factor C3a are compared immediately before the treatment and from about 1 to about 6 hours after start of the treatment.

Embodiment 11: The method of embodiment 9, wherein the levels of complement factor C3a are compared immediately before the treatment and after at least a week or about a month of treatment.

Embodiment 12: The method of any one of embodiments 1 to 11, wherein the levels of complement factor C5a does not significantly change.

Embodiment 13: The method of embodiment 12, wherein the levels of complement factor C5a are compared immediately before the treatment and after at least a week or about a month of treatment.

Embodiment 14: The method of any one of embodiments 1 to 13, further comprising administering a corticosteroid.

Embodiment 15: The method of embodiment 14, wherein the corticosteroid is prednisone.

Embodiment 16: The method of any one of embodiments 1 to 15, wherein the level of the complement factor after the treatment is within about 30%, about 20%, or about 10% of the level before the treatment.

Embodiment 17: A method of inhibiting C5aR in a human in need thereof, comprising administering to the human a therapeutically effective amount of avacopan:

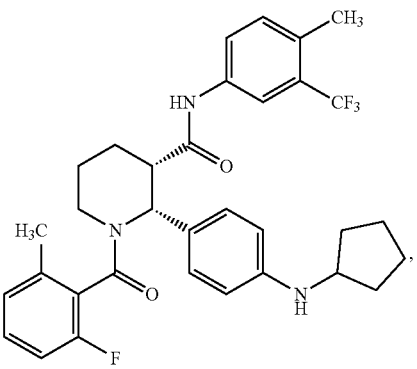 [SMILES: Cc1ccc(NC(=O)[C@H]2CCCN(C(=O)c3c(C)cccc3F)[C@H]2c2ccc(NC3CCCC3)cc2)cc1C(F)(F)F]

or a pharmaceutically acceptable salt thereof,
such that the level of plasma complement factor Bb, C3a, or C5a does not significantly change in the human upon C5aR inhibition.

Embodiment 18: The method of embodiment 17, comprising orally administering the avacopan or pharmaceutically acceptable salt thereof.

Embodiment 19: The method of embodiment 17 or 18, comprising administering avacopan.

Embodiment 20: The method of any one of embodiments 17 to 19, comprising administering about 30 mg avacopan.

Embodiment 21: The method of any one of embodiments 17 to 20, comprising administering the avacopan twice daily.

Embodiment 22: The method of any one of embodiments 17 to 21, comprising administering the avacopan for at least 12 weeks.

Embodiment 23: The method of any one of embodiments 17 to 22, wherein the level of the complement factor after the administration is within about 30%, about 20%, or about 10% of the level before the administration.

Embodiment 24: Avacopan or a pharmaceutically acceptable salt thereof for use in the treatment of ANCA-associated vasculitis in a human in need thereof wherein the level of plasma complement factor Bb, C3a, or C5a does not significantly change in the human upon treatment.

Embodiment 25: Avacopan or a pharmaceutically acceptable salt thereof for use according to embodiment 24, wherein Avacopan or a pharmaceutically acceptable salt is administered orally.

Embodiment 26: Avacopan or a pharmaceutically acceptable salt thereof for use according to embodiment 24 or 25, wherein about 30 mg of Avacopan is administered.

Embodiment 27: Avacopan or a pharmaceutically acceptable salt thereof for use according to any one of embodiments 24 to 26, wherein Avacopan is administered twice daily.

Embodiment 28: Avacopan or a pharmaceutically acceptable salt thereof for use according to any one of embodiments 24 to 27, wherein Avacopan is administered for at least 12 weeks.

Embodiment 29: Avacopan or a pharmaceutically acceptable salt thereof for use according to any one of embodiments 24 to 28, wherein the level of complement factor Bb does not significantly change.

Embodiment 30: Avacopan or a pharmaceutically acceptable salt thereof for use according to embodiment 29, wherein the levels of complement factor Bb are compared immediately before the treatment and after at least a week or about a month of treatment.

Embodiment 31: Avacopan or a pharmaceutically acceptable salt thereof for use according to embodiment 29 or 30, wherein the level of complement factor Bb before and after the treatment are from about 0.8 to 1.4 µg/mL.

Embodiment 32: Avacopan or a pharmaceutically acceptable salt thereof for use according to any one of embodiments 29 to 31, wherein the level of complement factor Bb after the treatment is within about 30%, about 20%, or about 10% of the level before the treatment.

Embodiment 33: Avacopan or a pharmaceutically acceptable salt thereof for use according to any one of embodiments 24 to 32, wherein the levels of complement factor C3a does not significantly change.

Embodiment 34: Avacopan or a pharmaceutically acceptable salt thereof for use according to embodiment 33, wherein the levels of complement factor C3a are compared immediately before the treatment and from about 1 to about 6 hours after start of the treatment.

Embodiment 35: Avacopan or a pharmaceutically acceptable salt thereof for use according to embodiment 33, wherein the levels of complement factor C3a are compared immediately before the treatment and after at least a week or about a month of treatment.

Embodiment 36: Avacopan or a pharmaceutically acceptable salt thereof for use according to any one of embodiments 33 to 35, wherein the level of complement factor C3a before and after the treatment are from about 25 to 100 ng/mL.

Embodiment 37: Avacopan or a pharmaceutically acceptable salt thereof for use according to any one of embodiments 33 to 36, wherein the level of complement factor C3a after the treatment is within about 30%, about 20%, or about 10% of the level before the treatment.

Embodiment 38: Avacopan or a pharmaceutically acceptable salt thereof for use according to any one of embodiments 24 to 37, wherein the levels of complement factor C5a does not significantly change.

Embodiment 39: Avacopan or a pharmaceutically acceptable salt thereof for use according to embodiment 38, wherein the levels of complement factor C5a are compared immediately before the treatment and after at least a week or about a month of treatment.

Embodiment 40: Avacopan or a pharmaceutically acceptable salt thereof for use according to embodiment 38 or 39, wherein the level of complement factor C5a before and after the treatment are from about 4 to 10 ng/mL.

Embodiment 41: Avacopan or a pharmaceutically acceptable salt thereof for use according to any one of embodiments 38 to 40, wherein the level of complement factor C5a after the treatment is within about 30%, about 20%, or about 10% of the level before the treatment.

Embodiment 42: Avacopan or a pharmaceutically acceptable salt thereof for use according to any one of embodiments 24 to 41, wherein ANCA-associated vasculitis in a human in need thereof is anti-MPO ANCA-associated vasculitis.

Embodiment 43: Avacopan or a pharmaceutically acceptable salt thereof for use according to any one of embodiments 24 to 41, wherein ANCA-associated vasculitis in a human in need thereof is anti-PR3 ANCA-associated vasculitis.

Embodiment 44: Avacopan or a pharmaceutically acceptable salt thereof for use according to any one of embodiments 24 to 43, wherein a corticosteroid is further administered.

Embodiment 45: Avacopan or a pharmaceutically acceptable salt thereof for use according to embodiment 44, wherein the corticosteroid is prednisone.

Embodiment 46: Avacopan or a pharmaceutically acceptable salt thereof for use according to any one of embodiments 24 to 45, wherein a CD20 inhibitor is further administered.

Embodiment 47: Avacopan or a pharmaceutically acceptable salt thereof for use according to embodiment 46, wherein the CD20 inhibitor is rituximab.

Embodiment 48: Avacopan or a pharmaceutically acceptable salt thereof for use according to any one of embodiments 24 to 47, wherein cyclophosphamide is further administered.

Embodiment 49: Avacopan or a pharmaceutically acceptable salt thereof for use in inhibiting C5aR in a human in need thereof, wherein the level of plasma complement factor Bb, C3a, or C5a does not significantly change in the human upon C5aR inhibition.

Embodiment 50: Avacopan or a pharmaceutically acceptable salt thereof for use according to embodiment 49, wherein Avacopan or a pharmaceutically acceptable salt is administered orally.

Embodiment 51: Avacopan or a pharmaceutically acceptable salt thereof for use according to embodiment 49 or 50, wherein about 30 mg of Avacopan is administered.

Embodiment 52: Avacopan or a pharmaceutically acceptable salt thereof for use according to any one of embodiments 49 to 51, wherein Avacopan is administered twice daily.

Embodiment 53: Avacopan or a pharmaceutically acceptable salt thereof for use according to any one of embodiments 49 to 52, wherein Avacopan is administered for at least 12 weeks.

Embodiment 54: Avacopan or a pharmaceutically acceptable salt thereof for use according to any one of embodiments 49 to 53, wherein the level of the complement factor after the administration is within about 30%, about 20%, or about 10% of the level before the administration.

V. Examples

Example 1: Effect of a Selective C5aR Antagonis, Avacopan, on Plasma Complement Levels in ANCA-Associate Vasculitis (AAV)

Methods

The CLEAR trial (Jayne D R W, et al. JASN 2017; 28:2756) compared 3 regimens in 67 patients with AAV: (1) full dose prednisone (60 mg daily, tapered); (2) avacopan 30 mg twice daily plus low dose prednisone (20 mg, tapered); (3) avacopan 30 mg twice daily plus no prednisone. All also received either cyclophosphamide or rituximab. There was a 12-week treatment period with 12 week follow-up period Plasma samples were collected from AAV patients who participated in CLEAR study at baseline and at 6 hour, Days 8, 29, and 85 during treatment. Plasma samples from 20 health controls matched for age, gender and ethnic background were collected at UNC Kidney Center.

EDTA whole blood was kept on ice immediately after collection and centrifuged at 4° C. for plasma preparation. Plasma samples were stored at −80° C. freezer until analysis for complement Bb, C5a, C5a, sC3b-9 and properdin by ELISA in one thaw.

Paired t-test was used for within group comparison and unpaired t-test was used for between group comparisons using log transformed data. P-values were corrected for multiple comparisons.

Results

Figure 5A:
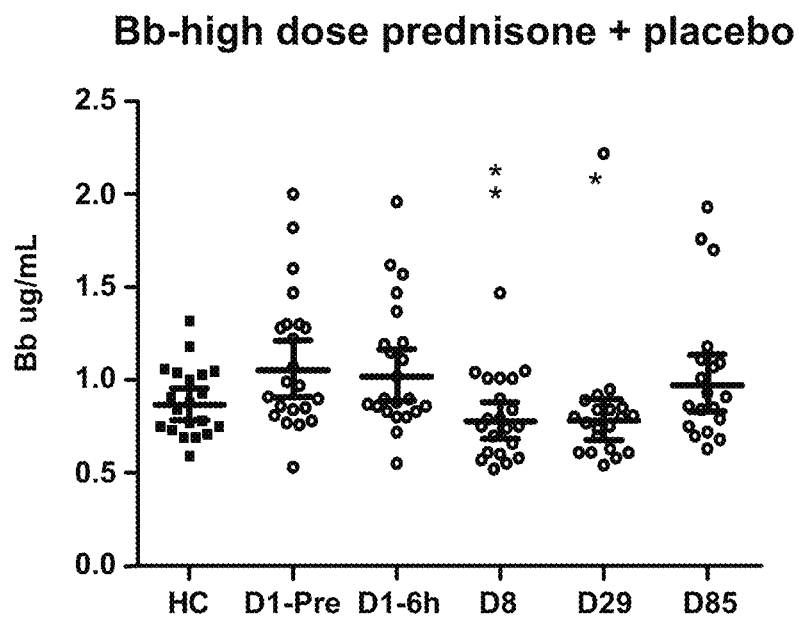
FIG. 5A-C plots the levels of complement factor Bb in patients receiving high dose prednisone (A), avacopan with low dose prednisone (B), and avacopan with no prednisone (C). The columns of the graphs display data points for healthy control patients (HC), and AAV patients at day 1 pretreatment (D1-Pre), six hours after treatment (D1-6 h), day 8 (D8), day 29 (D29), and day 85 (D85). These plots show that Bb levels decreased on days 8 and 29 in full dose prednisone group and rose again on day 85 when prednisone was tapered. No change in Bb levels observed during treatment in the two groups treatment with avacopan. *P<0.05; **P<0.01 compared to pre-dose within the group.
Figure 5B:
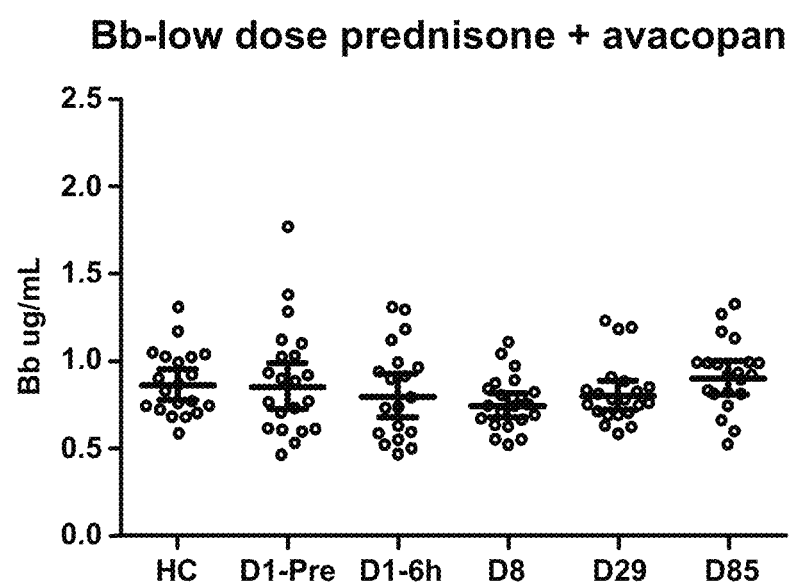
Figure 5C:
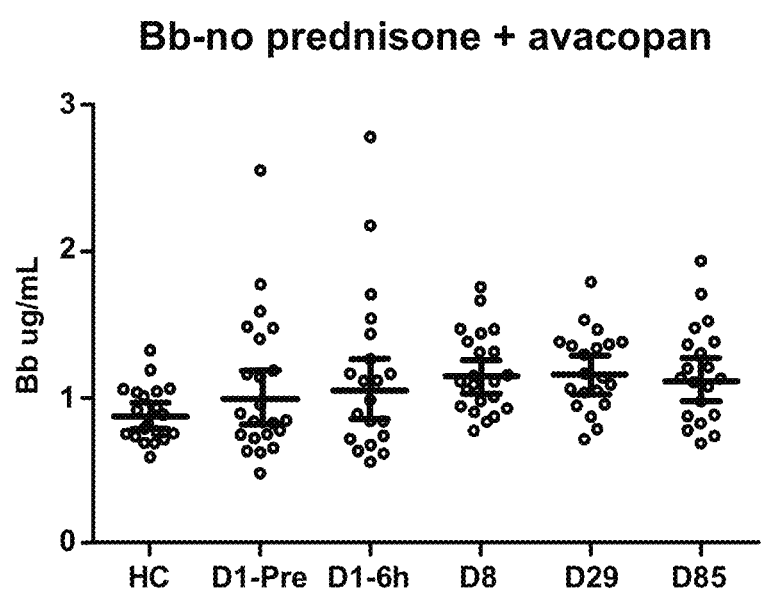
Figure 6A:
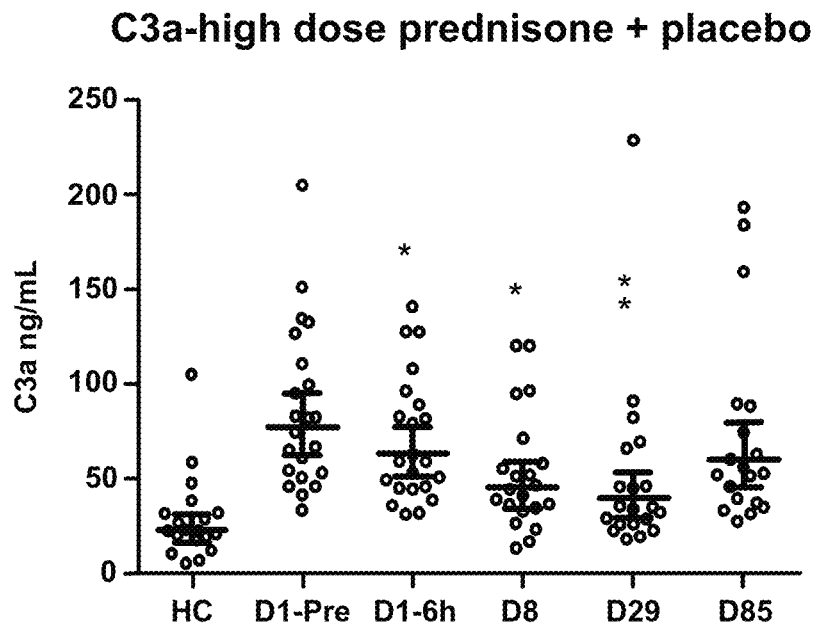
FIG. 6A-C plots the levels of complement factor C3a in patients receiving high dose prednisone (A), avacopan with low dose prednisone (B), and avacopan with no prednisone (C). The columns of the graphs display data points for healthy control patients (HC), and AAV patients at day 1 pretreatment (D1-Pre), six hours after treatment (D1-6 h), day 8 (D8), day 29 (D29), and day 85 (D85). These plots show that in full dose prednisone group C3a levels decreased as early as 6 hours and further decreased on days 8 and 29 and rose again on day 85 and rose again on day 85 when prednisone was tapered. No change in C3a levels observed in the group treated with avacopan without prednisone. *P<0.05, **P<0.01 compared to baseline within the group.
Figure 6B:
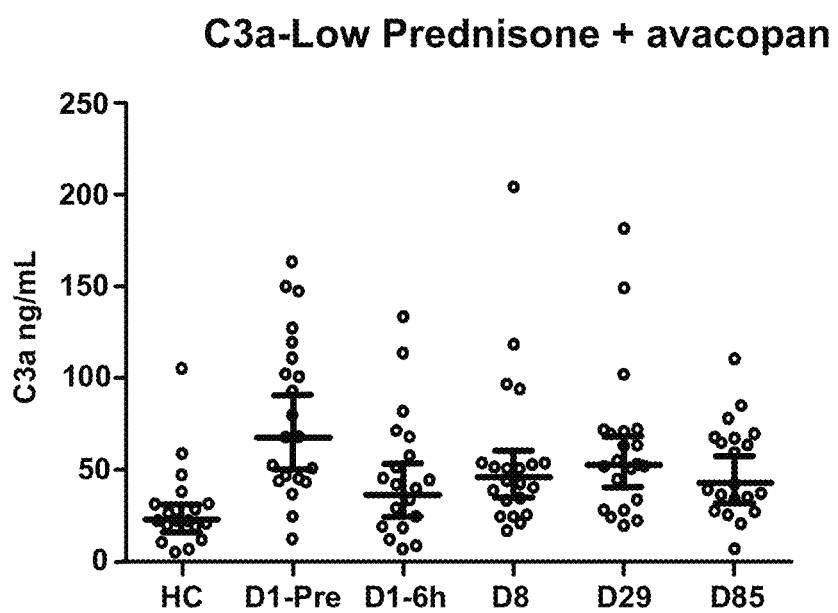
Figure 6C:
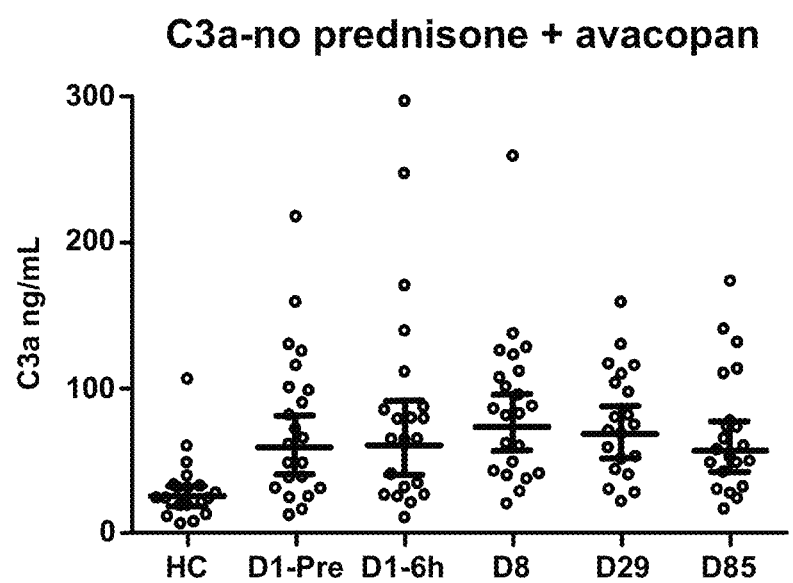
Figure 7A:
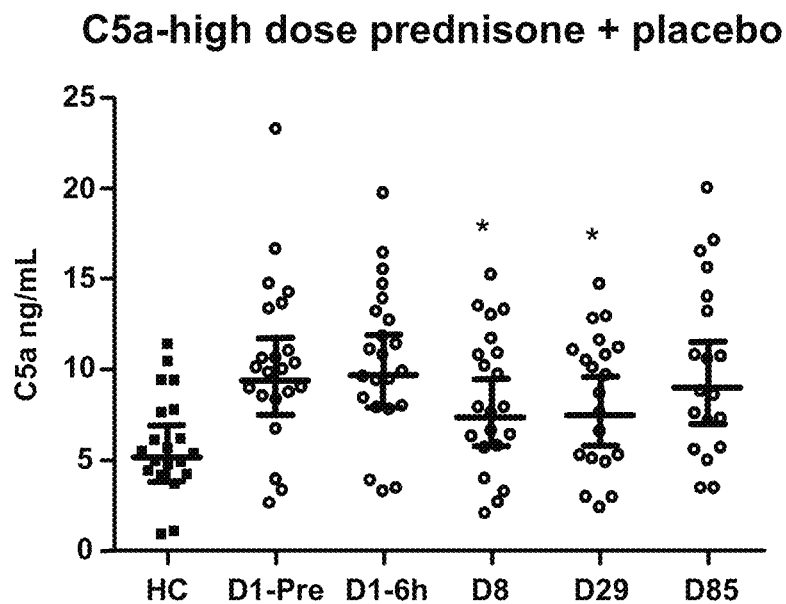
FIG. 7A-C plots the levels of complement factor C5a in patients receiving high dose prednisone (A), avacopan with low dose prednisone (B), and avacopan with no prednisone (C). The columns of the graphs display data points for healthy control patients (HC), and AAV patients at day 1 pretreatment (D1-Pre), six hours after treatment (D1-6 h), day 8 (D8), day 29 (D29), and day 85 (D85). In high dose prednisone groups, C5a decrease on day 8 and 29 and rose again on day 85 when prednisone was tapered. No change in C5a levels observed in the two groups treated with avacopan with low or noprednisone. *P<0.05, compared to baseline within the group.
Figure 7B:
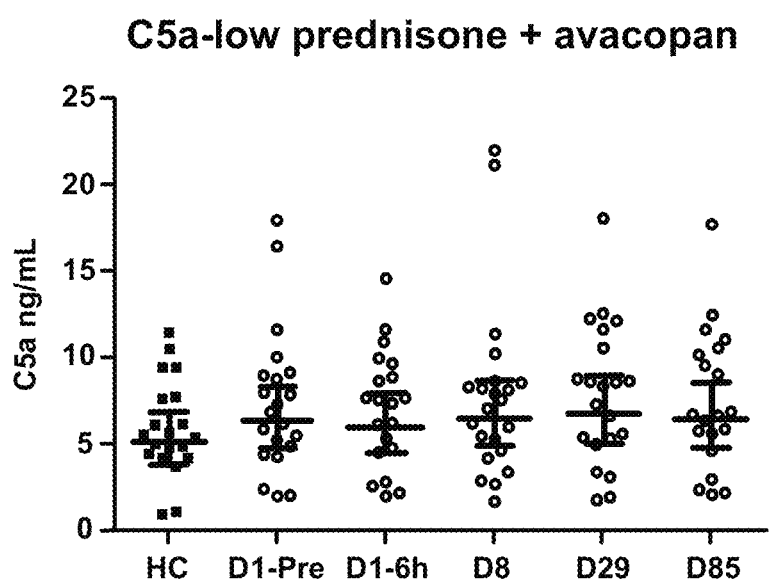
Figure 7C:
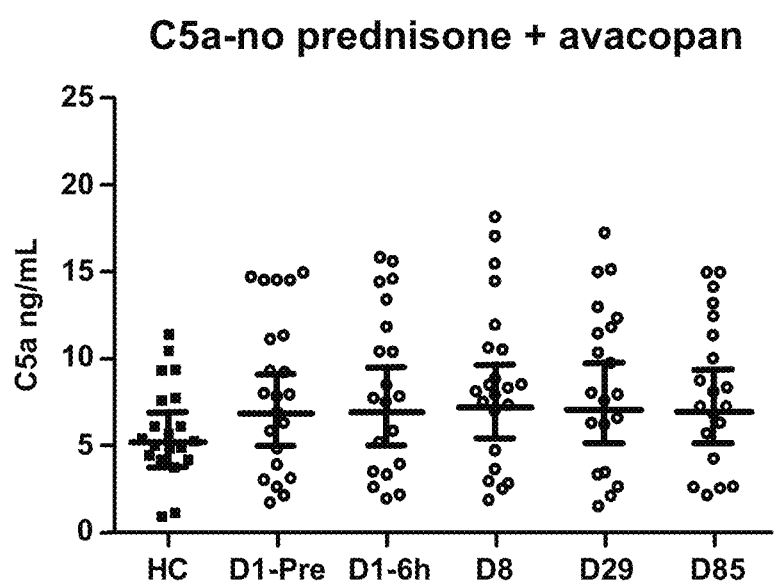
Figure 8A:
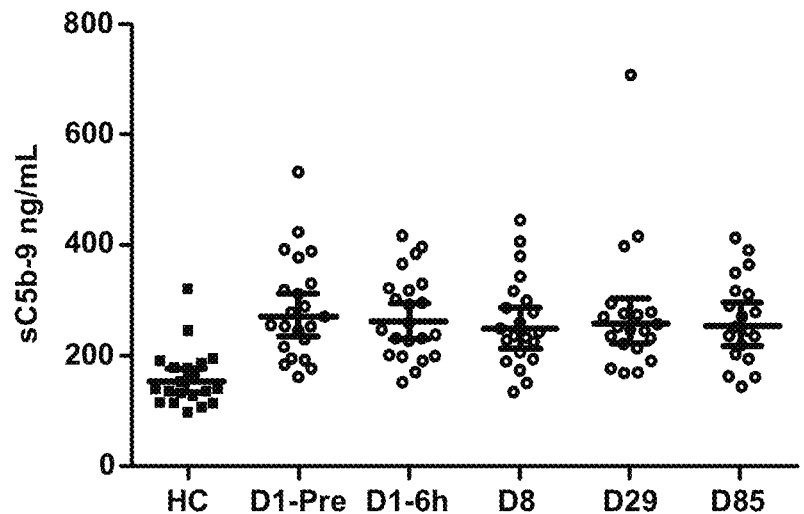
FIG. 8A-C plots the levels of sC5b-9 in patients receiving high dose prednisone (A), avacopan with low dose prednisone (B), and avacopan with no prednisone (C). The columns of the graphs display data points for healthy control patients (HC), and AAV patients at day 1 pretreatment (D1-Pre), six hours after treatment (D1-6 h), day 8 (D8), day 29 (D29), and day 85 (D85). No statistically significant changes in circulating sCD5-9 levels in any of the treatment groups were observed.
Figure 8B:
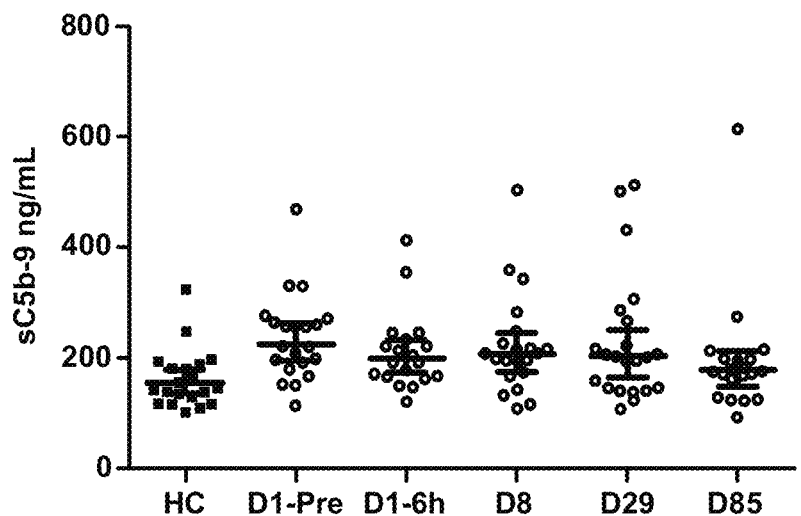
Figure 8C:
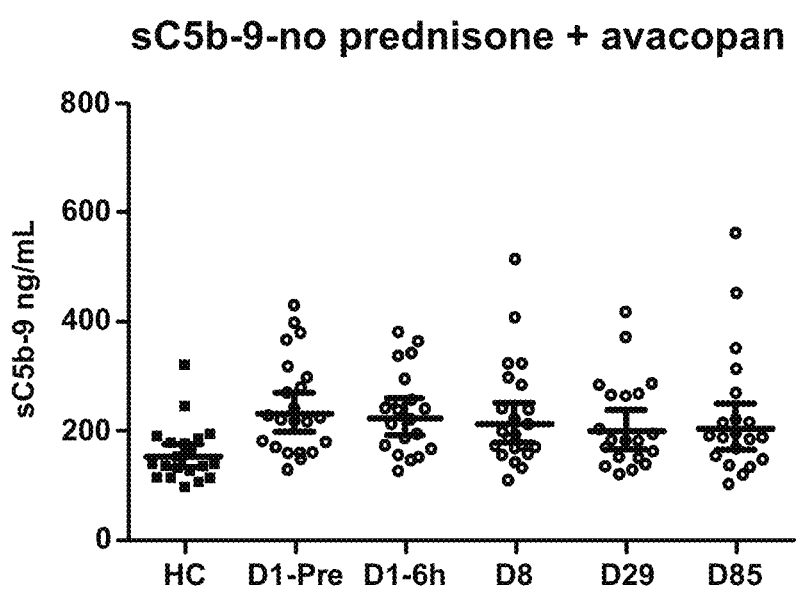
Figure 9A:
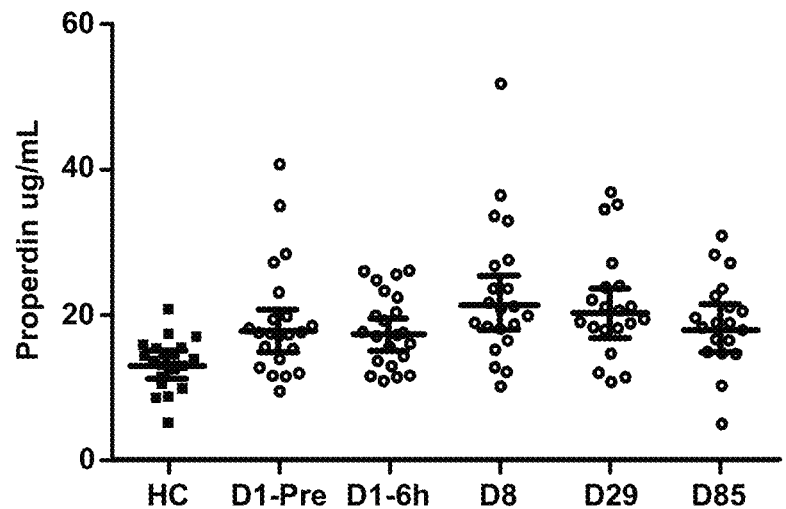
FIG. 9A-C plots the levels of properdin in patients receiving high dose prednisone (A), avacopan with low dose prednisone (B), and avacopan with no prednisone (C). The columns of the graphs display data points for healthy control patients (HC), and AAV patients at day 1 pretreatment (D1-Pre), six hours after treatment (D1-6 h), day 8 (D8), day 29 (D29), and day 85 (D85). No statistically significant changes in circulating properdin levels in any of the treatment groups were observed.
Figure 9B:
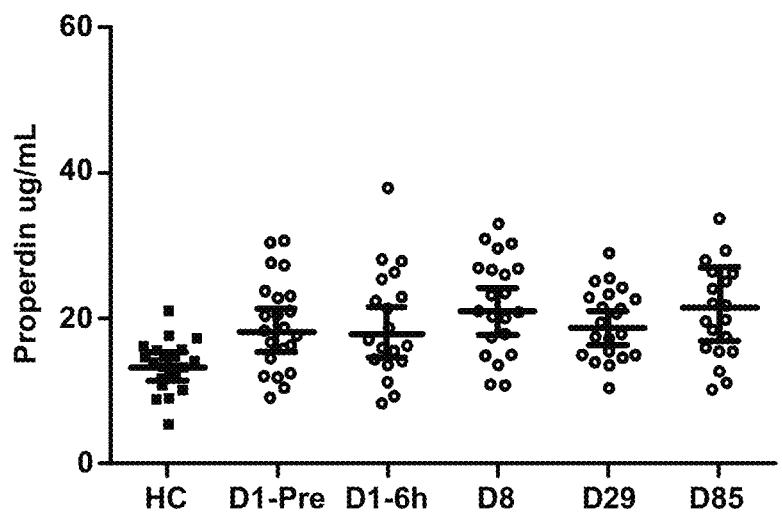
Figure 9C:
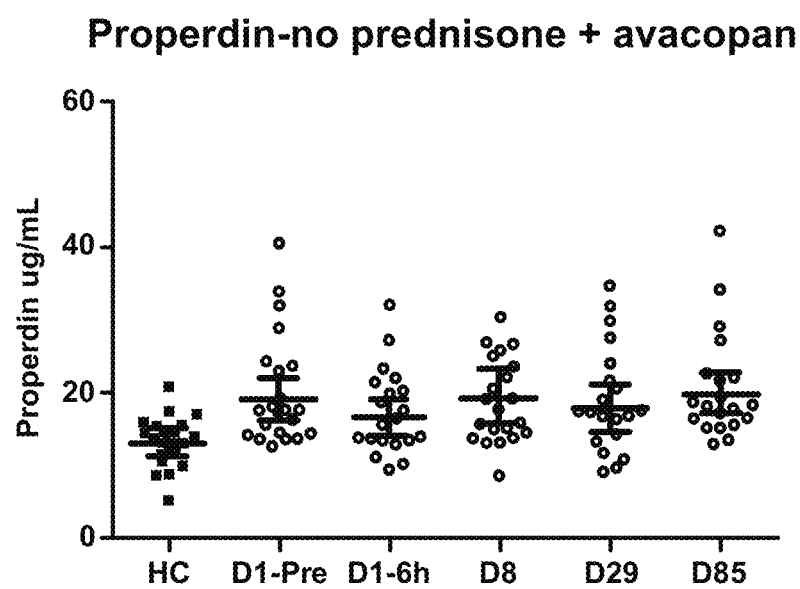

Before treatment, levels of C3a, C5a, sC5b-9 and properdin were significantly elevated in AAV patients compared to matched healthy controls (geomean [95%], C3a, 67.2 [57.5-78.7] vs 23.2 [16.9-31.9] ng/mL, p<0.001; C5a, 7.55 [6.50-8.78] vs 5.19 [3.87-6.95] ng/mL, p<0.05; sC5b-9, 241(222-262) vs 155(136-178) ng/mL, p<0.001; Properdin, 18.4 [16.9-20.0] vs 13.1 [11.4-15.6] µg/mL, p<0.001) (FIG. 4). In subjects treated with full dose prednisone, levels of Bb, C3a, and C5a decreased significantly on Day 8 and 29 rising again at day 85, coincident with tapering (FIG. 5A, FIG. 6A, FIG. 7A). In contrast, administration of avacopan did not impact circulating complement levels (FIG. 5B-C, FIG. 6C, FIG. 7B-C). There were no changes from baseline in mean plasma sC5b-9 or properdin levels in any treatment group (FIG. 8A-C & FIG. 9A-C). A summary of the results are provided in Table 1.

TABLE 1

Summary of Results

| Complement Factor | AAV vs. HC | Prednisone | Avacopan |
|---|---|---|---|
| Bb | Not Different | ↓ | No changes |
| C3a | ↑ | ↓ | No changes |
| C5a | ↑ | ↓ | No changes |
| sC5b-9 | ↑ | No changes | No changes |
| Properdin | ↑ | No changes | No changes |

Overall, AAV patients had high circulating levels of complement activation products when compared to healthy controls before treatment. Avacopan achieved clinical benefit in AAV without affecting the complement activation product levels in the 12 week treatment period. Prednisone was associated with transient reduction of up-stream complement activation.

CONCLUSIONS

Avacopan was associated with rapid improvement in AAV without an apparent impact on complement system. In particular, assembly of C5b-9 (the membrane attack complex) and upstream activities of the complement system important for host defense (e.g. bacterial infections) and tissue repair did not change upon administration of avacopan. In contrast, glucocorticoids were associated with dose-dependent reduction of circulating levels of upstream complement activation products.

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

What is claimed is:

1. A method of treating ANCA-associated vasculitis in a human having a reduced ability to fight infections, the method comprising administering to the human a therapeutically effective amount of avacopan:

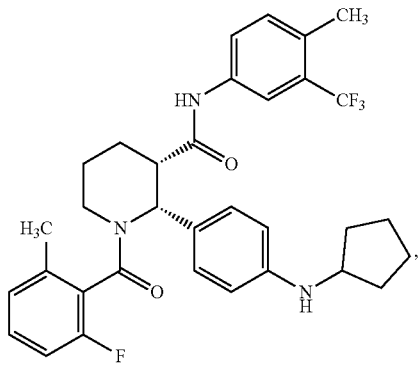 [SMILES: Cc1ccc(NC(=O)[C@H]2CCCN(C(=O)c3c(C)cccc3F)[C@H]2c2ccc(NC3CCCC3)cc2)cc1C(F)(F)F]

or a pharmaceutically acceptable salt thereof,
such that the level of plasma complement factor C5b-9 and C5a does not significantly change in the human upon treatment.

2. The method of claim 1, comprising orally administering avacopan.

3. The method of claim 1, comprising administering about 30 mg avacopan.

4. The method of claim 1, comprising administering the avacopan twice daily.

5. The method of claim 1, comprising administering the avacopan for at least 12 weeks.

6. The method of claim 1, wherein the level of complement factor Bb does not significantly change.

7. The method of claim 1, wherein the levels of complement factor C5a does not significantly change.

8. The method of claim 7, wherein the levels of complement factor C5a are compared immediately before the treatment and after at least a week or about a month of treatment.

9. The method of claim 7, wherein the level of complement factor C5a before and after the treatment are from about 4 to 10 ng/mL.

10. The method of claim 7, wherein the level of complement factor C5a after the treatment is within about 30%, about 20%, or about 10% of the level before the treatment.

11. The method of claim 1, ANCA-associated vasculitis in a human in need thereof is anti-MPO ANCA-associated vasculitis.

12. The method of claim 1, ANCA-associated vasculitis in a human in need thereof is anti-PR3 ANCA-associated vasculitis.

13. The method of claim 1, further comprising administering a corticosteroid.

14. The method of claim 13, wherein the corticosteroid is prednisone.

15. The method of claim 1, further comprising administering a CD20 inhibitor.

16. The method of claim 15, wherein the CD20 inhibitor is rituximab.

17. The method of claim 1, further comprising administering cyclophosphamide.

18. The method of claim 1, wherein the level of each complement factor after the administration is within about 30%, about 20%, or about 10% of the level before the administration.

19. A method of inhibiting C5aR in a human having a reduced ability to fight infections, comprising administering to the human a therapeutically effective amount of avacopan:

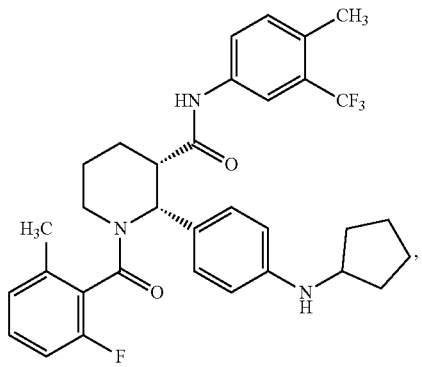 [SMILES: Cc1ccc(NC(=O)[C@H]2CCCN(C(=O)c3c(C)cccc3F)[C@H]2c2ccc(NC3CCCC3)cc2)cc1C(F)(F)F]

or a pharmaceutically acceptable salt thereof,
such that the level of plasma complement factor C5b-9 and C5a does not significantly change in the human upon C5aR inhibition.

20. The method of claim 19, comprising orally administering avacopan.

21. The method of claim 19, comprising administering about 30 mg avacopan.

22. The method of claim 19, comprising administering the avacopan twice daily.

23. The method of claim 19, comprising administering the avacopan for at least 12 weeks.

24. The method of claim 19, wherein the level of the complement factor after the administration is within about 30%, about 20%, or about 10% of the level before the administration.

* * * * *